United States Patent
Petrus

(10) Patent No.: US 6,573,299 B1
(45) Date of Patent: Jun. 3, 2003

(54) METHOD AND COMPOSITIONS FOR TREATMENT OF THE AGING EYE

(75) Inventor: Edward J. Petrus, Austin, TX (US)

(73) Assignee: Advanced Medical Instruments, Austin, TX (US)

(*) Notice: Subject to any disclaimer, the term of this patent is extended or adjusted under 35 U.S.C. 154(b) by 0 days.

(21) Appl. No.: 09/399,393

(22) Filed: Sep. 20, 1999

(51) Int. Cl.⁷ .............................................. A61K 31/20
(52) U.S. Cl. ....................................... 514/558; 514/912
(58) Field of Search ................................. 514/558, 912

(56) References Cited

U.S. PATENT DOCUMENTS

| | | |
|---|---|---|
| 3,856,941 A | 12/1974 | Turner |
| 4,296,130 A | 10/1981 | Herschler |
| 4,342,784 A | 8/1982 | Havemeyer et al. |
| 4,477,469 A | 10/1984 | Herschler |
| 4,708,965 A | 11/1987 | Morgan |
| 4,772,591 A | 9/1988 | Meisner |
| 4,863,748 A | 9/1989 | Herschler |
| 4,933,184 A | 6/1990 | Tsuk |
| 4,938,969 A | 7/1990 | Schinitsky et al. |
| 4,973,605 A | 11/1990 | Herschler |
| 5,071,878 A | 12/1991 | Herschler |
| 5,118,505 A | 6/1992 | Koltringer |
| 5,156,852 A | 10/1992 | La Haye et al. |
| 5,196,417 A * | 3/1993 | Dolling et al. ............ 514/226.5 |
| 5,229,130 A | 7/1993 | Sharma et al. |
| 5,238,933 A | 8/1993 | Catz et al. |
| 5,254,343 A | 10/1993 | Parah et al. |
| 5,266,594 A | 11/1993 | Dawson et al. |
| 5,281,722 A | 1/1994 | Blaschke et al. |
| 5,306,731 A | 4/1994 | Epstein |
| 5,310,764 A | 5/1994 | Baranowitz et al. |
| 5,334,612 A | 8/1994 | Kalden et al. |
| 5,409,693 A | 4/1995 | Perricone |
| 5,432,199 A | 7/1995 | Cavazza |
| 5,449,688 A | 9/1995 | Wahl et al. |
| 5,457,135 A | 10/1995 | Baranowitz et al. |
| 5,468,476 A | 11/1995 | Ahluwalia et al. |
| 5,470,874 A | 11/1995 | Lerner |
| 5,482,965 A | 1/1996 | Rajadhyaksha |
| 5,532,269 A | 7/1996 | Koltringer |
| 5,545,614 A | 8/1996 | Stamler et al. |
| 5,569,670 A | 10/1996 | Weischer et al. |
| 5,585,402 A | 12/1996 | Moncada et al. |
| 5,596,011 A | 1/1997 | Repine et al. |
| 5,620,980 A | 4/1997 | Samour |
| 5,643,587 A | 7/1997 | Scancarella et al. |
| 5,650,429 A | 7/1997 | Conrad et al. |
| 5,665,757 A | 9/1997 | Dunn et al. |
| 5,667,791 A | 9/1997 | Hersh et al. |
| 5,676,956 A | 10/1997 | Duffy et al. |
| 5,691,380 A | 11/1997 | Mason et al. |
| 5,723,451 A | 3/1998 | Majalli et al. |
| 5,728,735 A | 3/1998 | Ulrich et al. |
| 5,747,536 A | 5/1998 | Cavazza |
| 5,766,873 A | 6/1998 | Noble et al. |
| 5,780,693 A | 7/1998 | Bernhard et al. |
| 5,786,342 A | 7/1998 | Carpenter et al. |
| 5,789,396 A | 8/1998 | Blank et al. |
| 5,792,449 A | 8/1998 | Bryce-Smith |
| 5,804,594 A | 9/1998 | Murad |
| 5,807,957 A | 9/1998 | Samour et al. |
| 5,821,237 A | 10/1998 | Bissett et al. |
| 5,824,659 A | 10/1998 | Strickland et al. |
| 5,837,289 A | 11/1998 | Grasela et al. |
| 5,846,996 A | 12/1998 | Fallick |
| 5,871,769 A | 2/1999 | Fleming et al. |
| 5,873,831 A | 2/1999 | Bernstein et al. |
| 5,876,736 A | 3/1999 | Cohen et al. |
| 5,883,128 A * | 3/1999 | Yu et al. ..................... 514/557 |
| 5,886,042 A | 3/1999 | Yu et al. |
| 5,889,054 A | 3/1999 | Yu et al. |
| 5,897,891 A | 4/1999 | Godfrey |
| 5,916,912 A | 6/1999 | Ames et al. |
| 5,922,331 A | 7/1999 | Mausner |
| 5,922,346 A | 7/1999 | Hersh |
| 5,925,348 A | 7/1999 | Riley et al. |
| 5,925,620 A | 7/1999 | Ohlenschlager et al. |
| 5,937,790 A | 8/1999 | Ito et al. |
| 5,939,394 A | 8/1999 | Fleming et al. |
| 5,945,447 A | 8/1999 | Fallick |
| 6,103,756 A * | 8/2000 | Gorsek ....................... 514/458 |

OTHER PUBLICATIONS

Osborne DW, Henke JJ. Skin Penetration Enhancers Cited In the Technical Literature. *Pharmaceutical Technology* Nov. 1997 p 58–80.

Brechner RJ et al Ophthalmic Examination Among Adults With Diagnosed Diabetes Mellitus *JAMA* 1993 270(14)1714–18.

Rosenberg LA, Glaucoma; Early Detection and Therapy for Prevention of Vision Loss *American Family Physician* 1995 52(8) 2289–98.

Samples JR Pharmacologic Management of Glaucoma *Rational Drug Therapy* 1987 21(12)1–6.

Olson RJ, DeBry P, Zinc as a Treatment for Age–Related Macular Degeneration *J. Trace Elements in Experimental Medicine* 1998 11:137–145.

Mares–Pearlman J A et al. Assocation of Zinc and Antioxidant Nutrients With Age–Related Maculopathy. *Arch Ophthalmol* 1996 114:991–97.

(List continued on next page.)

Primary Examiner—Zohreh Fay

(57) ABSTRACT

This invention relates to a method for the prevention and treatment of orbital disorders associated with the aging eye in mammals by the application of a topical composition comprising a permeation enhancing amount of one or more penetration enhancers, and one or more bio-affecting agents which penetrate into the underlying tissues and into the vascular network of the orbit. Another object of this invention is the improvement of age-related changes to the eyelids such as dry skin, wrinkles, keratoses, age spots and pigmented skin lesions. It is a further object of this invention to prevent and treat cataract formation, glaucoma, diabetic retinopathy and macular degeneration.

5 Claims, No Drawings

OTHER PUBLICATIONS

Pratt SG, What We Now Know About AMD and Nutrition *Review of Ophthalmology* Aug. 1998 42–49.

Curcio C A, Millican C L. Basal Linear Deposit and Large Drusen are Specific for Early Age–Related Maculopathy. *Arch Ophthalmology* 1999 117:329–39.

Petrus EJ et al. Randomized, Double–Masked, Placebo–Controlled Clinical Study of the Effectiveness of Zinc Acetate Lozenges on Common Cold Symptoms in Allergy–Tested Subjects. *Current Therapeutic Research* 59(9) 595–607 1998.

Cuajungco MP, Lees GJ. Zinc Metabolism in the Brain: Relevance to Human Neurodegenerative Disorders. *Neurobiol Dis* 1997; 4(3–4) 137–69.

Chithra P et al. Influence of *Aloe vera* on the Glycosaminoglycans in the Matrix of Healing Dermal Wounds. *J. Ethnopharmacol* 1998 Jan. 59(3) 179–86.

Chithra P et al. Influence of *Aloe vera* on Collagen Turnover in Healing of Dermal Wounds in Rats. *Indian J. Exp Biol* 1998 Sep. 36(9) 896–901.

Heggers JP et al. Effect of the Combination of *Aloe vera*, Nitroglycerine, and L–Name on Wound Healing in the Rat Excisional Model. *J. Altern Complement Med.* 1997 Summer; 3(2): 149–153.

Kawada N, et al. Effect of Antioxidants, Resuenatrol, Quercetin, and NAC on the Functions of Cultured Rat Hepatic Stellate Cells and Kupffer Cells. *Hepatology*, 1998 May; 27(5):1265–74.

Tsai S H et al. Suppression of Nitric Oxide Synthase and the Down–Regulation of the Activation of NFkappa in Macrophages by Resuenatrol. *Br J. Pharmacol* 1999 Feb.; 126(3):673–80.

Sato M, et al. Contents of Resuenatrol, Piceid and Their Isomers in Commercially Available Wines Made From Grapes Cultivated in Japan *Biosci Biotechnol Biochem* 1997 Nov.; 61(11):1800–5.

Neufeld A H et al. Nitric–Oxide Synthase Inhibition Protects Rat Retinal Cells From Elevated IOP. *Proc Natl Acad Sci USA* 1999; 96:9944–9948.

\* cited by examiner

METHOD AND COMPOSITIONS FOR TREATMENT OF THE AGING EYE

FIELD OF THE INVENTION

A method and compositions for the prevention and treatment of orbital disorders associated with the aging eye.

BACKGROUND OF THE INVENTION

The eyes, usually the very first aspect noticed of a person's face, often show the earliest signs of the aging process. The aging process is ordinary first demonstrated by wrinkles of the eyelids, the need for glasses to correct for presbyopia, or visual loss associated with cataracts, glaucoma, diabetic retinopathy or macular degeneration.

Eyelids show age-related changes such as dry skin, wrinkles, keratoses, age spots and pigmented skin lesions. Dry eyelid skin appears dull and loses its radiance and is usually caused by low humidity, cold weather, contact pressure, detergents, solvents and some chemicals. A moisturizing topical lotion, cream or ointment usually restores the dry skin condition of the eyelids.

The skin of the upper and lower lids is unique in that it is the thinnest in the body, contains relatively little fat and subject to the most movement with blinking. Every layer of the skin changes dramatically with age. The epidermis and dermis become thinner and the density of elastic and collagen is reduced with aging. Wrinkles occur with a loss of subcutaneous fat so that the deeper layers of skin provide inadequate support for the epidermis and tiny folds appear which deepen with time.

Cataracts are the leading cause of blindness in the world, and the leading cause of reversible visual loss for persons over age 65. Cataracts are a loss of the transparency of the lens of the eye causing blurred vision, glare, sensitivity to light, poor night vision, halos around lights and color distortion. About 4 million persons have cataracts in the U.S. and 40,000 develop cataracts each year. With the life expectancy over 76 years, the incidence of cataracts is expected to double in the next 12 years. Cataract surgery is the most common surgical procedure for the elderly.

Glaucoma is the leading cause of irreversible blindness in the world, the second most common cause of irreversible blindness in the U.S. and the most common cause of blindness among blacks. An estimated 2.5 million persons in the U.S. have glaucoma. Glaucoma is not a single disease, but rather a group of disorders that damage the optic nerve. Samples J R, *Rational Drug Therapy* 1987; 21(12):1–6. Rosenberg L F, *American Family Physician* 1995;52(8):2289–2298.

Diabetes is the fourth leading cause of death affecting almost 16 million Americans, a third of them undiagnosed, costing over $100 billion per year, 15% of U.S. health-care dollars. Some 800,000 new cases of diabetes develop every year. By the year 2030, the number could reach 50 million here and at least 300 million worldwide. Diabetes mellitus is the leading cause of new blindness among persons 20 to 74 years of age in the United States. Retinopathy begins to develop soon after the diagnosis of insulin-dependent diabetes mellitus (IDDM), and after 15 years, the prevalence is almost 100%. One million people in the U.S. have IDDM or Type I diabetes. In non-insulin-dependent diabetes (NIDDM) or Type II diabetes, currently 15 million, about 21% of the patients have retinopathy at diagnosis, and 60% after 20 years. Type II diabetics have tripled over the last 30 years, and involves half of Americans over the age of 65. Proliferative retinopathy occurs in 10–20% of NIDDM. Brechner R J, et al, *JAMA* 1993;270:1714–1718.

Macular degeneration, or age-related macular degeneration (AMD), affects the central part of the retina and is the leading cause of blindness in people over age 65 in the U.S. AMD affects 13 million people and causes impairment in about 1.2 million. About 30% of patients over 75 have AMD, and 23% of the remainder will develop it within five years. The prevalence of AMD increases with age from 16.8% in patients 55–64 to 25.6% in patients 65–74 and up to 42% in patients over 75. There currently is no known cure for dry or atrophic AMD, the form characterized by hard or soft drusen (deposits of cellular debris), changes in the retinal pigment epithelium (RPE), or atrophy of photoreceptors and RPE. This form accounts for approximately 90% of all cases. The remainder of AMD cases have the "wet" form characterized by neovascularization and exudation. Pratt S G, *Review of Ophthalmology August* 1998:42–50.

SUMMARY OF THE INVENTION

This invention relates to a method for the prevention and treatment of orbital disorders associated with the aging eye in mammals by the application of a topical composition comprising a permeation enhancing amount of one or more penetration enhancers, and one or more bio-affecting agents which penetrate into the underlying tissues and into the vascular network of the orbit. Another object of this invention is the improvement of age-related changes to the eyelids such as dry skin, wrinkles, keratoses, age spots and pigmented skin lesions. It is a further object of this invention to prevent and treat cataract formation, glaucoma, diabetic retinopathy and macular degeneration.

DETAILED DESCRIPTION OF THE INVENTION

Oxidative stress, or the predominance of free radicals over antioxidant mechanisms, has been implicated in premature aging, heart disease, arthritis, cancer, Alzheimer's disease and ocular disorders such as cataracts, glaucoma, diabetic retinopathy and macular degeneration. Free radicals are very unstable and highly reactive. They try to capture electrons from other molecules to gain stability, a process known as oxidation. They are unpaired oxygen molecules that cause cellular damage and are generated by a combination of light and oxygen or during reperfusion after an ischemic insult that deprives the eye of oxygen and nutrition. Free radicals occur naturally and cannot be avoided. Inadequate dietary intake of antioxidants can result in oxidative stress which can produce major derangement of cell metabolism, causing extensive damage to DNA, proteins and lipids.

Antioxidants are substances that significantly delay or inhibit oxidation. They neutralize free radicals by supplying electrons. Antioxidants protect from free radicals by inhibiting free radical formation, intercepting free radicals, and repairing free radical-induced injury. Antioxidant defenses involve both enzymatic and non-enzymatic systems. The enzymatic defense system includes superoxide dismutase, catalase, and glutathione peroxidase. Non-enzymatic defense systems include vitamins C and E.

The eye and the skin are the only organs of the body normally exposed to light. The eye is specifically adapted to respond to a certain band of electromagnetic wavelengths known as visible light. Infrared and ultraviolet wavelengths elicit no visual response but, nevertheless, enter the eye and may produce heating and photobiological changes. Short wavelengths are more damaging than longer wavelengths for a given total amount of energy absorbed. "Glassblowers cataract" presents as posterior capsular opacities resulting from heat absorption. The retina in the phakic eye is normally protected from short light wavelengths (under 400nm) by the crystalline lens, but after cataract surgery it is exposed to UV light.

The formation of cataracts is associated with several biochemical changes in the lens of the eye: decreased levels of antioxidants ascorbic acid and glutathione, increased lipid, amino acid and protein oxidation, increased sodium and calcium, loss of amino acids and decreased lens metabolism. The lens, which lacks blood vessels, is suspended in extracellular fluids in the anterior part of the eye. Nutrients, such as ascorbic acid, glutathione, vitamin E, selenium, bioflavonoids and carotenoids are required to maintain the transparency of the lens. Low levels of selenium results in an increase of free radical-inducing hydrogen peroxide, which is neutralized by the selenium-dependent antioxidant enzyme glutathione peroxidase. Lens-protective glutathione peroxidase is also dependent on the amino acids methionine, cysteine, glycine and glutamic acid.

Cataracts can also develop due to an inability to properly metabolize galactose found in dairy products that contain lactose, a disaccharide composed of the monosaccharide galactose and glucose. Cataracts can be prevented, delayed, slowed and possibly even reversed if detected early and metabolically corrected.

Retinal damage is attributed to free radical initiated reactions in glaucoma, diabetic retinopathy and age-related macular degeneration (AMD). The eye is a part of the central nervous system and has limited regenerative capability. The retina is composed of numerous nerve cells which contain the highest concentration of polyunsaturated fatty acids (PFA) and subject to oxidation. Free radicals are generated by UV light entering the eye and mitochondria in the rods and cones, which generate the energy necessary to transform light into visual impulses. Free radicals cause peroxidation of the PFA by hydroxyl or superoxide radicals which in turn propagate additional free radicals. The free radicals cause temporary or permanent damage to retinal tissue.

Glaucoma is usually viewed as a disorder that causes an elevated intraocular pressure (IOP) that results in permanent damage to the retinal nerve fibers, but a sixth of all glaucoma cases do not develop an elevated IOP. This disorder is now perceived as one of reduced vascular profusion and an increase in neurotoxic factors. Recent studies have implicated elevated levels of glutamate, nitric oxide and peroxynitirite in the eye as the causes of the death of retinal ganglion cells. Neuroprotective agents may be the future of glaucoma care. For example, nitric oxide synthase inhibitors block the formation of peroxynitrite from nitric oxide and superoxide. In a recent study, animals treated with aminoguanidine, a nitric oxide synthase inhibitor, had a reduction in the loss of retinal ganglion cells. It was concluded that nitric oxide in the eye caused a cytotoxicity in many tissues and neurotoxicity in the central nervous system. Neufeld, AH, et al, *Proc Natl Acad Sci USA* 1999;96:9944–9948.

Diabetic retinopathy occurs when the underlying blood vessels develop microvascular abnormalities consisting primarily of microaneurysms and intraretinal hemorrhages. Oxidative metabolites are directly involved with the pathogenesis of diabetic retinopathy and free radicals augment the generation of growth factors that lead to enhanced proliferative activity. Nitric oxide produced by endothelial cells of the vessels may also cause smooth muscle cells to relax an result in vasodilation of segments of the vessel. Ischemia and hypoxia of the retina occur after thickening of the arterial basement membrane, endothelial proliferation and loss of pericytes. The inadequate oxygenation causes capillary obliteration or nonperfusion, anteriolar-venular shunts, sluggish blood flow and an impaired ability of RBCs to release oxygen. Lipid peroxidation of the retinal tissues also occurs as a result of free radical damage.

The macula is responsible for our acute central vision and composed of light-sensing cells (cones) while the underlying retinal pigment epithelium (RPE) and choroid nourish and help remove waste materials. The RPE nourishes the cones with the vitamin A substrate for the photosensitive pigments and digests the cones shed outer tips. RPE is exposed to high levels of WV radiation, and secretes factors that inhibit angiogenesis. The choroid contains a dense vascular network that provides nutrients and removes the waste materials.

In AMD, the shed cone tips become indigestible by the RPE, where the cells swell and die after collecting too much undigested material. Collections of undigested waste material, called drusen, form under the RPE. Photoxic damage also causes the accumulation of lipofuscin in RPE cells. The intracellular lipofuscin and accumulation of drusen in Bruch's membrane interferes with the transport of oxygen and nutrients to the retinal tissues, and ultimately leads to RPE and photoreceptor dysfunction. Curcio C A, Millican C L, *Arch Ophthalmol* 1999;1 17:329–339. In exudative AMD, blood vessels grow from the choriocapillaris through defects in Bruch's membrane and may grow under the RPE, detaching it from the choroid, and leaking fluid or bleeding.

Macular pigment, one of the protective factors that prevents sunlight from damaging the retina, is formed by the accumulation of nutritionally derived carotenoids, such as lutein, the fatty yellow pigment that serves as a delivery vehicle for other important nutrients and zeaxanthin. Antioxidants such as vitamins C and E, β-carotene and lutein, as well as zinc, selenium and copper, are all found in the healthy macula. In addition to providing nourishment, these antioxidants protect against free radical damage that initiates macular degeneration.

The components of the method and composition of the present invention will be discussed separately because no prior art embraces them as a solitary method or composition to prevent and treat orbital disorders of the aging eye with a topical composition. The topical composition of the present invention comprises one or more penetration enhancers and one or more bio-affective agents.

Penetration Enhancer

The present invention uses a penetration enhancer or permeation enhancer to increase the permeability of the skin to a pharmacologically active agent to increase the rate at which the drug diffuses through the skin and enters the tissues and bloodstream. A chemical skin penetration enhancer increases skin permeability by reversibly altering the physiochemical nature of the stratum corneum to reduce its diffusional resistance.

The skin of the upper and lower lids consists of a thin epidermis that is constantly replenished. The next layer is the dermis that contains nerves, blood and lymph vessels, sweat and sebaceous glands and hair follicles. Hair follicles on the skin can act as shunts to bring the composition from the skin and into the body part. Surrounding these structures are elastic and collagen fibers that give strength and flexibility. Below the dermis is a layer of connective tissue and fat cells that form the subcutaneous layer. Blood flows posteriorly from the lids and usually forms two veins, the superior and inferior ophthalmic veins that form the central retinal vein and also flow into the cavernous sinus which enters into the circulation. Bio-affecting agents penetrate the skin and are absorbed into the tissues and vascular network.

In a review of the technical and patent literature up to 1996, more than 275 different chemical compounds were found to be cited as skin penetration enhancers. Most of the compounds are generally recognized as safe (GRAS) ingredients that would often be considered inert by a formulator. Osborne D W, Henke J J, *Pharmaceutical Technology*, Nov. 1997, pp 58–86. The compounds cited in the article are incorporated by reference. Examples of penetration enhancers include: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof.

A number of patents disclose the use of penetration enhancers to deliver medications transdermally. Grasela et al, U.S. Pat. No. 5,837,289, discloses the use of at least two separate penetration enhancers in a cream to deliver an extensive list of medications. Catz et al, U.S. Pat. No. 5,238,933, discloses a skin permeation enhancer composition comprising a lower aliphatic ester of a lower aliphatic carboxyl acid in combination with a lower alkanol to administer an active agent. Sharma et al, U.S. Pat. No. 5,229,130, discloses a vegetable oil-based skin permeation enhancer to deliver active agents through the skin. Tsuk, U.S. Pat. No. 4,933,184, discloses a transderrnal composition that uses methanol either sequentially or simultaneously to deliver drugs. Havemeyer et al, U.S. Pat. No. 4,342,784, discloses a method of topically administering a gel with DMSO and carboxy polymethylene resin with a neutralizing agent to enable the skin salt to break down the gel to release the DMSO. Rajadhyaksha, U.S. Pat. No. 5,482,965, discloses a transdermal composition containing a dioxane. Samour, U.S. Pat. Nos. 5,620,980, 5,807,957, discloses the use of a dioxolane and urethane to treat hair loss. None of the above cited patents teach or suggest the use of the method or composition outlined in the present invention.

Eyelid Preparation

The composition according to the present invention for topical application contains active ingredients that prepare the epidermis of the skin to receive the bio-affecting agents. Alpha hydroxy acid (AHA) and beta hydroxy acid (BHA) are exfoliants that work to smooth skin and assist cell turnover. AHAs work partly by sloughing off dead cells on the skin surface and are best for sun damage or a thickened outer layer of skin. AHAs also thicken underlying layers and increase the amount of hyaluronic acid, a gelatinous substance that cements cells together, thus smoothing out fine lines on the skin surface. AHAs may be derived from natural fruit sources and contain a high amount of lactic acid, but may also contain glycolic acid, citric acid, malic acid, decanoic acid, octanoic acid, tartaric acid or pyruvic acid.

Other forms of AHAs include; ammonium glycolate, alpha-hydroxyethanoic acid, anunonium alpha-hydroxyethanoate, alpha-hydroxyoctanoic acid, alpha-hydroxycaprylic acid and hydroxycaprylic acid. AHAs thicken the skin, particularly the epidermis and increase ground substance in the dermis. AHAs are effective in eradicating most age spots, relieve dry skin and decrease wrinkles. AHA range is between 5% to 10%, with a pH of 3–4.

BHAs can cut through the lipid layer of skin, helping skin to shed cells and loosen plugs in the pores. Natural sources of BHA include salicylic acid and wintergreen leaves. BHA range is 1% to 2% and works best at a pH of 3 to 4. Alpha or beta hydroxy acids may be present as free acids, or as peroxides, lactones, amides, esters or salts of organic or inorganic bases. The composition of the invention can be formulated as a foundation cream or liquid or paste makeup base to be applied to the skin.

A number of patents disclose the use of exfolients and other ingredients to treat aging skin. Parah et al, U.S. Pat. No. 5,254,343, discloses a method for decreasing the effects of steroids with the addition of AHA. Yu et al, U.S. Pat. Nos. 5,886,042 and 5,889,054, disclose a composition comprising an amphoteric agent, AHA or alpha ketoacid for treating a skin condition. Scancarella et al, U.S. Pat. No. 5,643,587, discloses a composition to treat skin discoloration around the eyes comprising a live yeast cell extract, magnesium ascorbyl phosphate, tocopherol acetate and retinol palmitate. Duffey et al, U.S. Pat. No. 5,676,956, discloses a composition to treat eye puffiness comprising a yeast cell extract, magnesium, ascorbyl phosphate, tocopherol acetate and retinol palmitate. Cohen et al, U.S. Pat. No. 5,876,736, discloses a cosmetic makeup composition to revitalize skin consisting of a film forming agent, sunscreen agent, exfoliating agent, moisturizing agent, liposome vesicles and antioxidant. None of the above cited patents teach or suggest the use of the method or composition outlined in the present invention.

Bio-affecting Agents

The present invention relates to novel compositions for topical application and delivery of bio-affecting agents through the protective outer layer of the skin, into the underlying tissues and into the vascular network of the targeted body part. The term "bio-affecting agent" refers to any chemical substance or formulation which beneficially affects the body. The bio-affecting agents of the preferred composition comprises; lutein, zeaxanthin, nitric oxide synthase inhibitors, resveratrol, alpha hydroxy avid, beta hydroxy acid, N-acetylcysteine, ascorbityl palmitate, ascorbic acid, alpha-lipoic acid, glutathione, methyl-sulfonyl-methane, zinc compounds, aloe vera, antioxidants, vitamins, minerals, amino acids, and mixtures thereof, and other active agents to form a solution, suspension, cream, ointment, gel, film, or spray.

The concentration of the bio-affecting agents in the composition can also vary greatly and will be dependent upon may factors, e.g. type, bioavailability, potency, surface area to which it is applied, composition used and the amount of the penetrating agents used. The concentration of bio-affecting agents will vary from about 0.1% to 40% of the total composition, and may be suspended or dissolved.

A wide variety of therapeutic agents, known to provide beneficial effects when absorbed into the tissues and vascular network, in combination with a penetration enhancer, facilitates penetration through the skin and absorbed into the vascular network of the targeted body parts. This topical administration offers a significant advantage over oral administration of therapeutic agents by overcoming the difficulty of poor gastrointestinal absorption, by using a lower dosage than required orally, and allows more of the active agents to provide therapeutic relief. Bio-affective agents to be used in the composition includes some of the following:

Lutein and Zeaxanthin

Carotenoids are phytonutrients which include α-carotene, β-carotene, cryptoxanthin, lycopene, lutein and zeaxanthin. Aging eyes have a decreased amount of carotenoids, which cannot be manufactured in humans. The retina contains two main carotenoids, lutein and zeaxanthin in the macula, which offer the strongest protection against AMD. The foveal part of the retina (a depression in the center of the macula) has a yellow pigmentation that is composed primarily of lutein and zeaxanthin. Zeaxanthin is a mixture of two stereoisomers, one of which is converted from lutein. Zeaxanthin protects the retina by absorbing UV light, blocks the activity of peroxide radicals, inhibits LDL oxidation and consequently protects cell membranes from this and other free radical damage.

Lutein, an antioxidant nutrient, is found in most fruits and vegetables, particularly dark green leafy vegetables like spinach, kale, parsley and collard greens. Lutein filters out blue light from the retina and prevents oxidative stress or free radical damage in the macula. Lutein can be converted to zeaxanthin in the blood serum and is the key carotenoid for providing the proper amount of lutein and zeaxanthin in the retina. A diet of 6 mg of lutein per day led to a 43% lower prevalence of AMD. Lutein and zeaxanthin work by accumulating in the macula. The present invention uses a topical dose of 2–3 mg of lutein per day to provide similar benefits.

The use of carotenoids is well known in the art. Baranowitz et al, U.S. Pat. Nos. 5,310,764 and 5,457,135, disclose a method for preventing and treating AMD with β-carotene. Bernstein et al, U.S. Pat. No. 5,873,831, discloses a method for measuring macular carotenoid levels. Bernhard et al, U.S. Pat. No. 5,780,693, discloses a process for the production of zeaxanthin from lutein. None of the above cited patents teach or suggest the use of the method and composition outlined in the present invention.

Nitric Oxide Synthase Inhibitors

Nitric oxide is a short lived, gaseous free radical that is synthesized from the terminal guanidino nitrogen of L-arginine in an oxidation reaction catalyzed by NOS. NOS expression is inducible by endotoxin, cytokines, growth factor and immune complexes. The overexpression of NOS may result from increased levels of tumor necrosis factor-α (TNF-α), IL-1β, and other proinflammatory cytokines. Nitric oxide plays an important role in autoimmunity and inflammation. NSAIDs, such as aspirin, and to a lesser extent, sodium salicylate, resveratrol, zinc compounds and tetracycline inhibit the expression of NOS protein.

Nitric oxide synthase inhibitors which may be employed in this invention include, but are not limited to: arginine-based analogues such as methylated arginines, substituted L-arginine, nitro-arginine, L-$N^G$-nitroarginine , $N^G$-monomethyl-L-arginine (NMA), N-nitro-L-arginine methyl ester, N-amino-L-arginine, N-methyl-L-arginine, $N^G$-monomethyl-L-arginine (L-NMA), L-$N^G$-monomethyl-arginine (L-NMMA); flavoprotein binders such as diphenylene iodonium and related iodonium derivatives, ornithine and ornithine derivatives such as N-imino-ethyl-L-ornithine; tetracycline; L-canavanine; citrulline; redox dyes such as methylene blue; calmodulin binders such as trifluoropiperazine and calcinarin; heme binders; resveratrol; zinc compounds; tetrahydropterin analogs such as aminoguanidine; and depleters of biopterin such as methotrexate.

Resveratrol (3,5,4'-trihydroxystilbene), an antioxidant found in wine, can inhibit the action of cyclo-oxygenase and lipo-oxygenase enzymes and inhibit the release of pro-inflammatory eicosanoids, leukotrienes and platelet aggregation promoters. Sato M, el al *Biosci Biotechnol Biochem* 1997 Nov;61(11):1800–5. Resveratrol also suppresses nitric oxide synthase. Tsai SH, et al, *Br. J Pharmacol* 1999 Feb;126(3):673–80. Resveratrol was shown to inhibit tumor necrosis factor-alpha (TNF-alpha) and nitric oxide production. Kawada N Hepatology 1998 May;27(5): 1265–74. Resveratrol dosage range is 5 to 10 mg per day or 250 mg as a lyophilized grape extract. Topical dosage range is 2 to 3 mg.

The use of NOS inhibitors is well known in the art. Cavazza, U.S. Pat. Nos. 5,432,199 and 5,747,536, discloses the use of L-carnitine and resveratrol to treat peripheral vascular diseases and peripheral diabetic neuropathy or acetyl D-camitine to treat glaucoma. Dawson et al, U.S. Pat. No. 5,266,594, discloses a method of preventing or treating glutamate neurotoxicity with a NOS inhibitor capable of penetrating the blood brain barrier. Ahluwalia et al, U.S. Pat. No. 5,468,476, discloses a method of reducing hair growth with a NOS inhibitor. Wahl et al, U.S. Pat. No. 5,449,688, discloses a method for treating chronic inflammatory conditions by parenterally or intravenously administering a NOS inhibitor. Stamler et al, U.S. Pat. No. 5,545,614, discloses a method for stimulating skeletal muscle contractions with a NOS inhibitor. Moncada et al, U.S. Pat. No. 5,585,402, discloses a method for inhibiting tissue damage by using a NOS inhibitor to decrease NO production in vascular endothelial cells. Dunn et al, U.S. Pat. No. 5,665,757, discloses a method for treating anxiety using a NOS inhibitor. Mjalli et al, U.S. Pat. No. 5,723,451, discloses a method for inhibiting NOS using one of eleven formulations. None of the above cited patents teach or suggest the use of the composition and method outlined in the present invention.

Anti-inflammatory Agents

Inflammation is a fundamental pathologic process involving complex reactions that occur in the affected blood vessels and adjacent tissues in response to an injury or abnormal stimulation caused by a physical, chemical, or biologic agent. The acute inflammatory response begins after cellular injury due to microorganisms, physical agents (such as bums, radiation, and trauma), chemicals, necrotic tissue, and immunological reactions. Five classic signs are manifested in acute inflammation; redness, heat, pain and loss of function. These signs are induced by changes which take place in the microvasculature (arterioles, capillaries, and venules) and the interstitial areas (fluid-filled regions between cells and tissues). These include changes in vascular flow and caliber, changes in vascular permeability, and leucocyte exudation. The first change involves vasodilation of the vessels and increased blood flow. The second change involves increased permeability of the blood vessels with a movement of fluid and proteins out of the vessels creating edema of the tissues. The final change occurs as white blood cells infiltrate and accumulate in the surrounding tissue. The increased blood flow and permeability of the microvascular system at the inflamed body part facilitates treatment to the area by using a penetration enhancer to deliver the bio-affective agents.

The spread of the acute inflammatory response following injury to a small area of tissue suggests that chemical substances are released from injured tissues, spreading outwards into uninjured areas. These chemicals, called endogenous chemical mediators, cause vasodilation, emigration of neutrophils, chemotaxis and increased vascular permeability. Histamine is a chemical mediator in acute inflammation and causes vascular dilatation and vascular permeability. It is stored in mast cells, basophil and eosinophil leucocytes, and platelets. Histamine release is stimulated by complement components C3a and C5a and by lysosomal proteins released from neutrophils. Prostaglandins are a group of long-chain fatty acids derived from arachidonic acid. They increase vascular permeability, and platelet aggregation. Drugs such as aspirin and NSAIDs inhibit one of the enzymes involved in prostaglandin synthesis. Other chemical mediators include; leukotrienes, serotonin and lymphokines. Plasma contains four enzymatic cascade systems; complement, the kinins, the coagulation factors and the fibrinolytic system.

Chronic inflammations are characterized by a longstanding dull pain, and indurated swelling, and the presence of granulation tissue. The predominant cells seen in chronic inflammation are the mononuclear leukocytes, such as macrophages, lymphocytes, and plasma cells. A fibroblastic proliferation is seen more often than a fluid exudate.

Inflammation accelerates the aging process and is believed responsible for many of the changes that occur in the aging eye. Some bio-affective agents of the present invention with anti-inflammatory properties are the following:

N-acetylcysteine

The present invention uses N-acetylcysteine (NAC), an amino acid required by our bodies to produce glutathione, with antioxidant properties capable of reducing inflammatory and catabolic molecules. Inflammation causes the release of arachidonic acid which generates leukotrienes (LTs) which are mediators of ischemia, epithelial destruction and arterial constriction. LTs are produced by many cell types such as, mast cells, leucocytes, connective tissue cells, macrophages, alveolar cells and vascular smooth muscle cells. In addition to NAC, other derivatives of amino acids cysteine and cystine include: N,N'-acetylcystine (N-DAC) and N-acetyl homocysteine (NAH). NAC, N-DAC, NAH interact with peroxides and LTs, reducing toxic free radicals, interrupt the LT cascade and reduce inflammation and promote healing. When NAC is given along with ascorbic acid and glutathione, the results are synergistic. The oral dosage range of NAC is 400 to 600 mg per day. The topical dosage range is 100 to 200 mg.

The use of NAC is well known in the art. Morgan, U.S. Pat. No. 4,708,965, discloses a method of treating the herpes virus with a compound comprising N-DAC, NAH and NAC. Epstein, U.S. Pat. No. 5,306,731, discloses a method for treating or preventing glaucoma by administering NAC. Repine et al, U.S. Pat. No. 5,596,011, discloses a method for treating macular degeneration with a glutathione enhancing agent, and antioxidant and an anti-inflammatory agent, interferon. Mason et al, U.S. Pat. No. 5,691,380, discloses a composition comprising an organopolysiloxane, NAC and an emulsifier. Noble et al, U.S. Pat. No. 5,766,873, discloses a method for inhibiting cell damage with NAC. Bissett et al, U.S. Pat. No. 5,821,237, discloses a topical skin composition comprising a cyclic polyanonic polyol, surfactant and NAC. Fleming et al, U.S. Pat. No. 5,871,769, discloses a method for the prevention and treatment of diabetes mellitus consisting of magnesium gluconate, and an antioxidant such as NAC. None of the above cited patents teach or suggest the use of the method and compositions outlined in the present invention.

Ascorbyl Palmitate/Ascorbic Acid

One preferred composition combines ascorbyl palmitate as a synthetic ester of vitamin C, which is fat soluble, has a neutral pH, is extremely stable and compatible with many creams, lotions and oils, and is non-irritating when applied to the skin. Since it is fat soluble, it penetrates the skin more readily and reaches high levels in a short period of time. Skin pretreated with topical ascorbyl palmitate in a lecithin gel base had decreased erythema after exposure to UVB when compared to untreated skin. A 5% lotion of ascorbyl palmitate was effective in reducing erythema from UV injured skin.

Vitamin C is the main antioxidant in skin and can be 80% depleted after 45 minutes exposure to UV radiation which generates free radicals and reactive oxygen species and activates an aracidonic acid metabolism, a mediator of inflammation, within the skin. Topical ascorbyl palmitate acts as a powerful anti-inflammatory agent within the cell, and stimulates collagen production and fibroblasts. Because ascorbyl palmitate resides within the cell membrane due to its fat solubility, it acts synergistically with vitamin E, it can regenerate the vitamin E radical as opposed to ascorbic acid which only acts at the cell interface. Long term high intake, greater than 1,000 mg/day of ascorbic acid (vitamin C) has been linked with a substantially reduced risk of cataracts. Ascorbic acid dosage range is 200 to 1,000 mg per day. Topical dosage range is 1 to 5 percent.

The use of ascorbyl palmitate and ascorbic acid is well known in the art. Perricone, U.S. Pat. No. 5,409,693, discloses a method to treat sunburn skin with a composition of ascorbyl palmitate and vitamin E in a lecithin base. Lemer, U.S. Pat. No. 5,470,874, discloses a composition of ascorbic acid and proanthocyanidine for topical application. Fallick, U.S. Pat. No. 5,846,996, discloses a composition for treating damaged skin with ascorbic acid and glutathione. Mausner, U.S. Pat. No. 5,922,331, discloses a skin cream composition comprising ascorbic acid, tocopherol, glycerol ester and other complexes in microcapsule. Ito et al, U.S. Pat. No. 5,937,790, discloses a method and feed composition for inhibiting stress proteins in blood comprising L-ascorbic acid-2-mono-phosphoric acid and antioxidants. Fallick, U.S. Pat. No. 5,945,447, discloses a topical preparation of ascorbic acid, polyethylene glycol and silicone or vegetable oil. Meissner, U.S. Pat. No. 4,772,591, discloses a method for wound healing comprising ascorbic acid, calcium, tyrosine and phenylalanine and anti-inflammatory amino acids. Schinitsky et al, U.S. Pat. No. 4,938,969, discloses a method to treat wrinkles comprising ascorbic acid, tyrosine and a zinc salt. Murad, U.S. Pat. No. 5,804,594, discloses an oral composition for skin conditions. None of the above cited patents teach or suggest the use of the method and compositions outlined in the present invention.

Alpha-Lipoic Acid

Alpha-lipoic acid (ALA) is a potent antioxidant and anti-inflammatory agent that is both water and fat soluble making it the universal antioxidant. The present invention uses ALA as an anti-inflammatory agent because of its effect within the cell. A 1% lotion can decrease fine wrinkles, boost levels of vitamins C and E, and act as a neuroprotective agent. ALA dosage range is 10 to 600 mg, but usually 25 to 300 mg. Topical dosage range is 1 to 2%.

The use of alpha-lipoic acid is well known in the art. Koltringer, U.S. Pat. Nos. 5,118,505, 5,532,269, discloses a composition for nerve fiber diseases and circulation disturbances comprising ginkgo bilobae extract, folic acid, alpha-lipoic acid and vitamin-B groups. Blaschke et al, U.S. Pat. No. 5,281,722, discloses a preparation and use of pure salts of alpha-lipoic acid. Kalden et al, U.S. Pat. No. 5,334,612, discloses a pharmaceutical composition containing alpha-lipoic acid for treating retrovirus disorders. Weischer et al, U.S. Pat. No. 5,569,670, discloses a method of treating diabetes mellitus comprising alpha-lipoic acid and vitamin E and salts. Conrad et al, U.S. Pat. No. 5,650,429, discloses a method for treating circulatory disorders with alpha-lipoic acid in reduced or oxidized form or a tromethamol salt. Urich et al, U.S. Pat. No. 5,728,735, discloses compositions of alpha-lipoic acid for inflammatory disorders. None of the above cited patents teach or suggest the use of the method or compositions outlined in the present invention.

Glutathione

Glutathione is a protein composed of three amino acids, glycine, glutamic acid and cysteine. High levels of glutathione are found in the lens of the eye and levels decrease as cataracts form. Glutathione is also effective in preventing macular degeneration. The usual oral dose of L-glutathione is 100–200 mg. In accordance with the present invention a topical dosage range of 25 to 50 mg is recommended.

The use of glutathione is well known in the art. Blank et al, U.S. Pat. No. 5,789,396, discloses a composition for regulating skin wrinkles or atrophy comprising salicylic acid, an antioxidant or radical scavenger as glutathione and a carrier. Hersh, U.S. Pat. Nos. 5,667,791 and 5,922,346, discloses a composition for reducing free radical damage comprising reduced glutathione, selenium and carriers. Riley et al, U.S. Pat. No. 5,925,348, discloses a dietary composition for treatment of aging skin using methyltransferase from an extract of sacred lotus seed containing ascorbic acid and glutathione. Ames et al, U.S. Pat. No. 5,916,912, discloses a method for increasing the metabolic rate of aged cells with an oral dietary composition of carnitine and antioxidant as glutathione. Ohlenschlager et al, U.S. Pat. No. 5,925,620, discloses a composition consisting of reduced glutathione and anthrocyanin. Fleming et al, U.S. Pat. No. 5,939,394, discloses a composition comprising magnesium gluconate and antioxidants as glutathione. None of the above cited patents teach or suggest the use of the method and compositions outlined in the present invention.

Methyl-Sulfonyl-Methane

Methyl-sulfonyl-methane (MSM) or dimethyl sulfone is essentially DMSO with an extra oxygen molecule and lacks the lipid-solubility of DMSO, but can be coupled with another penetration enhancer. In the body, MSM gives up its sulfuir to form methionine and cysteine for connective tissue. MSM is anti-inflammatory and penetrates deep within the skin's surface to moisturize, soften and rejuvenate dry, aging, or damaged skin. The therapeutic dosage range for MSM is 2–10 grams orally per day. The recommended topical dosage range of the present invention is 1–5 grams.

Numerous patents for MSM were filed by Herschler. U.S. Pat. Nos. 4,296,130, discloses a method for softening skin; 4,477,469 discloses a composition of MSM and carbamide to soften skin; 4,863,748 discloses a method for adding sulfuir to the diet with MSM; 4,973,605 discloses a method for treating muscle cramps associated with arthritis with oral MSM; and 5,071,878 discloses a method for using MSM in a diet for sulfur and health reasons. None of the above cited patents teach or suggest the use of the method and composition outlined in the present invention.

Zinc Compounds

Zinc compounds have anti-inflammatory and anti-infective properties. In a published article, Petrus EJ et al., Current Therapeutic Research, 1998; 59(9): 595–607, the inventor served as chief investigator and discussed the benefits and effects of zinc compounds, particularly for the aging eye.

Zinc is an essential trace element in human biology that is known to be necessary for many biologic functions, such as growth, appetite, testicular maturation, skin integrity, mental activity, wound healing, and imunune system maintenance. Approximately 300 enzymes are known to require zinc for their activities. Zinc deficiency in humans is widespread and is more prevalent in areas where the population subsists on cereal proteins.

Zinc has been shown to be an essential element for the function of the immune system. Regarding the effect of zinc on allergies, it is known that mast cells have been implicated as mediators of Type I allergic reactions. Mast cell derived reactions result from the release of histamine, heparin, prostaglandins, SRS-A, and various vasoactive amines from granules on the surface of mast cells, possibly including kinins. The inhibitory effect of zinc on histamine release from mast cells are attributed to its action on the stabilization of the mast cell membrane. Zinc ions were found to stabilize cell plasma membranes and prevent induced histamine and vasoactive amine release from tissue mast cells. It has been observed that unsequestered zinc ions (4 to 20 millimolar) are released in inflammation from mast cell granules suggesting a common linkage with inflammation. Zinc is a competitive antagonist of the calcium-dependent IgE and f-met peptide mediated histamine release from human basophils and suggested that zinc compounds might be considered for the treatment of autoimmune disorders.

Zinc compounds are acknowledged as anti-inflammatory agents, as astringents and beneficial in wound healing, and have antimicrobial, antifungal and antiviral activity. Zinc is the active agent in formulations to treat skin disorders, decubitus ulcers, abrasions, and has a tightening effect on sagging or loose skin. Zinc stabilizes the cell membranes and inhibits the formation of free radicals. Zinc also strengthens the integrity of blood vessel walls by reducing the membrane permeability and stopping bleeding. Unlike other metals, zinc is virtually nontoxic.

Zinc supplements have been used as a treatment for AMD. A growing body of evidence indicates that macular degeneration is driven by light-induced oxidizing damage suggesting that antioxidant enzyme systems could be important in slowing the progress of this disease. Two enzymes, superoxide dismutase and catalase share zinc as a common cofactor. A study published in 1988 concluded that zinc supplements improved AMD, and that the zinc group remained stable and showed less accumulation of drusen. Olson R J, DeBry P, Zinc as a treatment for Age-Related Macular Degeneration, J of *Trace Elements in Experimental Medicine* 1998; 1 1:137–145.

Zinc was not a common ingredient in supplements before 1978. Only 5% of people in this population reported taking supplements containing zinc between 1978 and 1980. The retina is susceptible to oxidative damage and that retinal damage can be modulated by the presence of antioxidant nutrients and zinc. Zinc may play a role in oxidant defense as a cofactor required for the activity of the enzymes. Zinc plays a role in numerous biochemical systems outside of oxidant defense that might also influence retinal integrity. A clinical trial using high-dose zinc supplementation reported a reduction in the loss of visual acuity in patients with AMD. The results of a multicenter case-control study suggest that high intakes of carotenoids, particularly lutein and zeaxanthin lowered the risk for advanced neovascular AMD. Mares-Perlman J A et al, Association of zinc and antioxidant nutrients with age-related maculopathy *Arch Ophthalmol* 1996;114:991997.

Zinc is also a very potent inhibitor of nitric oxide synthase (NOS). Cuajungco M P, Lees G J *Neurobiol Disease* 1997;4 (3–4):137–69. The dosage range of an oral zinc compound is 30 to 60 mg per day in divided doses. The suggested topical dosage range of the present invention is 10 to 20 mg per day. Zinc compounds are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

The use of zinc compounds is well known in the art. Turner, U.S. Pat. No. 3,856,941, discloses a process of preparing an astringent gel. Bryce-Smith, U.S. Pat. No. 5,792,449, discloses a composition of zinc linoleate to treat skin disorders, and that zinc is readily absorbed into the skin. La Haye et al, U.S. Pat. No. 5,156,852, discloses a method for the prevention of AMD with an oral composition of antioxidants, cofactors for activating metalloenzymes and glutathione elevating compounds. Godfrey, U.S. Pat. No. 5,897,891, discloses an oral composition comprising a zinc compound, amino acid and copper compound. The above cited patent does not teach or suggest the use of the method and composition outlined in the present invention.

Aloe Vera Extract

Aloe vera has been well reported to have anti-inflammatory properties. The present invention uses aloe vera of various-sized polysaccharide molecules. It is believed that smaller molecules reduce inflammation, act as intercellular antioxidants and have direct antibacterial and antiviral effects, while larger molecules modulate the immune system. Both topical and oral treatments with aloe vera were found to increase the synthesis of glycosaminoglycans and enhance would healing. Chithra P, Sajithlal G B, Chandrakasan G, Influence of Aloe vera on the glycosaminoglycans in the matrix of healing dermal wounds in rats. *J Ethnopharmacol* 1998 Jan;59(3):179–86. Aloe vera also increased the biosynthesis of collagen. Chithra P, Sajithlal G B, Chandrakasan G, Influence of Aloe vera on collagen turnover in healing of dermal wounds in rats. *Indian J Exp Biol* 1998 Sep;36(9):896–901. Aloe vera mixed with a nitric oxide inhibitor (L-NAME) improved wound healing and prevented dermal ischemia by reversing the effects of thromboxane synthase. Effect of the combination of Aloe vera, nitroglycerin, and L-NAME on wound healing in the rat excisional model. *J Altern Complement Med* 1997 Summer;3(2):149–53.

The use of Aloe vera is well known in the art. Carpenter et al, U.S. Pat. No. 5,786,342, discloses a method of reducing symptoms associated with chronic respiratory diseases using acetylated mannan from aloe vera. Strickland et al, U.S. Pat. No. 5,824,659, discloses the use of a oligosaccharide from Aloe to inhibit the loss of skin immunocompetency from ultraviolet irradiation. None of the above cited patents teach or suggest the use of the method and composition outlined in the present invention.

Other active components may be added to the composition to achieve the desired therapeutic effects to the aging eye. Some of the active components include: Vitamin A and its various salts, vitamin B complex containing $B_1$, $B_2$, $B_3$, $B_5$, $B_6$, $B_{12}$, bioflavenoids, vitamin E, folic acid, pyruvate, tyrosine, phenylalanine, dimethylaminoethanol, ubiquinones, boron, calcium, chromium, copper, iodine, magnesium, manganese, molybdenum, lycopene, taurine, rutin, biotin, glycine, malic acid, skin whiteners, lecithin and herbal products.

Compositions of the present invention may also include various additives, such as, water, alcohols, oils (mineral, vegetable, animal and synthetics), glycols, preservatives, antioxidants, amino acids, stabilizers, surfactants, emollients, anti-infective agents, adjuvants, thickening and gelling agents, anthocyanidins, proanthocyanidins, amino sugars, glycosaminoglycans, colorants, gums, esters, hormones, silicones, polymers, fragrances, sunscreens, acids, bases, buffers, vitamins, minerals, salts, polyols, proteins and their derivatives, essential oils, other enzymes, co-enzymes and extracts, detergents, soaps, anionics, non-ionics, ionics, waxes, lipids, fillers, celluloses, amines, thickeners, sugars, manganese, magnesium, histidine, herbal derivatives, and the like, so long as such additives do not defeat the objectives of the present invention.

The use of a topical, as opposed to an oral or parenteral form of the bio-affective agents offers major advantages: they deliver a very high concentration of the bio-affective agents to the desired site; eliminate the possibility of gastrointestinal upset or ulcers and low potential for drug interactions. This invention is further illustrated by the following examples which are to be regarded as illustrative only, and in no way limit the scope of the invention. The above-mentioned patents are hereby incorporated by reference.

TABLE 1

| Bio-Affecting Agents | Adult Daily Oral Dosage | Adult Daily Topical Dosage |
|---|---|---|
| Lutein | 6 mg | 2–3 mg |
| Zeaxanthin | 2–3 mg | 1–2 mg |
| Resveratrol | 5 mg | 2–3 mg |
| N-acetylcysteine | 400–600 mg | 100–200 mg |
| Ascorbic acid | 200–1,000 mg | 50–250 mg |
| Ascorbyl palmitate | 100–800 mg | 25–200 mg |
| Alpha-lipoic acid | 25–300 mg | 10–100 mg |
| Glutathione | 100–200 mg | 25–50 mg |
| Methyl-sulfonyl-methane | 2–10 gm | 1–5 gm |
| Zinc sulfate | 30–60 mg | 10–20 mg |
| Tocopherol complex | 200–800 mg | 50–200 mg |
| Selenium | 200–400 mcg | 50–100 mcg |
| Vitamin A | 5,000–50,000 IU | 1,000–20,000 IU |
| Beta-carotene | 30–180 mg | 10–50 mg |

Table 1 shows the recommended daily oral dosage for some of the bioaffecting agents and the suggested topical dosage for achieving the same benefits to the affected body part.

EXAMPLE 1

| Topical Eyelid Gel | |
|---|---|
| Lutein | 0.5% |
| Zeaxanthin | 0.2% |
| Resveratrol | 1.0% |
| Methyl-sulfonyl-methane | 1.2% |
| Retinyl palmitate | 0.2% |
| Zinc lineolate | 2.0% |
| Ascorbyl palmitate | 4.0% |
| Tocopherol acetate | 0.5% |
| Alpha-lipoic acid | 1.0% |
| Glutathione | 0.2% |
| Vitamin B complex | 0.2% |
| Selenomethionine | 0.1% |
| Acetyl L-carnitine HCl | 0.1% |
| Copper gluconate | 0.1% |
| Manganese gluconate | 0.1% |
| Tyrosine | 1.0% |
| Phenylalanine | 1.0% |
| Calcium pantothenate | 1.0% |
| EDTA | 0.1% |
| Alpha hydroxy acid | 3.0% |
| Carboxyvinyl polymers | 2.0% |
| Aloe vera gel | 1.0% |
| Propylene glycol | 3.0% |
| Ethanol | 1.0% |
| Methyl paraben | 0.2% |
| Propyl paraben | 0.1% |
| Glycerin | 2.0% |
| Water | 73.2% |

The topical eyelid gel in Example 1 provides benefits when applied to the eyelid surface. The composition may also be incorporated into cosmetics, which to some may be considered a "cosmeceutical" a product that combines some of the properties of each.

EXAMPLE 2

| Topical Eyelid Cream | |
|---|---|
| Lutein | 0.5% |
| Zeaxanthin | 0.2% |
| Resveratrol | 1.0% |
| Methyl-sulfonyl-methane | 1.2% |
| Retinyl palmitate | 0.2% |
| Zinc lineolate | 2.0% |
| Ascorbyl palmitate | 4.0% |
| Tocopherol acetate | 0.5% |
| Alpha-lipoic acid | 1.0% |
| Glutathione | 0.2% |
| Vitamin B complex | 0.2% |
| Selenomethionine | 0.1% |
| Acetyl L-carnitine HCl | 0.1% |
| Copper gluconate | 0.1% |
| Manganese gluconate | 0.1% |
| Tyrosine | 1.0% |
| Phenylalanine | 1.0% |
| Calcium pantothenate | 1.0% |
| EDTA | 0.1% |
| Histidine | 0.5% |
| Alpha hydroxy acid | 3.0% |
| Carboxyvinyl polymers | 2.0% |
| Aloe vera gel | 1.0% |
| Propylene glycol | 3.0% |
| Silicone oil | 2.0% |
| Ethanol | 1.0% |
| Methyl paraben | 0.2% |
| Propyl paraben | 0.1% |
| Water | 72.7% |

The cream in Example 2 is applied to the eyelid and may use zinc oxide or silicone oil to achieve a cream or mixed with a cosmetic base.

EXAMPLE 3

An 84 year old lady with wrinkles and loose eyelid skin, early cataract formation and macular degeneration. Her initial visual acuity, with correction, was 20/50 OD and 20/60 OS, with drusen and pigment dispersion in the macular area. She was started on the gel in Example 1, to be applied twice a day. After one week, she had a cosmetic improvement of her lids with some decrease in wrinkles and tightening of the eyelid skin. After three months, she had a slight improvement in the visual acuity of her left eye to 20/40. Her condition remained stable after six months.

EXAMPLE 4

A 54 year old male with early baggy eyelids, wrinkles at the orbital rim and early diabetic retinopathy. His visual acuity was 20/40 OD and 20/25 OS with correction. He was started on the cream in Example 2 to use on the eyelids in the evening and prior to retiring. After one week he noticed a reduction of the wrinkles and after two weeks a tightening of the eyelids. After four months the visual acuity of the right eye improved to 20/30. His status remained stable after six months of treatment.

EXAMPLE 5

A 61 year old lady with wrinkles of the eyelids and gradual loss of visual acuity due to cataracts. Her initial visual acuity was 20/30 OD and 20/25 OS and progressed to 20/50 OD and 20/40 OS three months later. She was started on the gel in Example 1, to use on her eyelids twice a day. She had an improvement of her wrinkles and baggy eyelids after two weeks. She had no further loss of visual acuity after eight months of therapy.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A method for the treatment of orbital disorders, selected from a group consisting of cataracts, glaucoma, diabetic retinopathy and macular degeneration, associated with the aging eye in mammals, by the application of a topical composition comprising at least one penetration enhancer and at least one alpha hydroxy acid, in a therapeutically acceptable vehicle, so that the delivery of bio-affecting agents through the protective outer layer of the skin, into the underlying tissues and into the vascular network of the targeted body part to reduce inflammation and provide relief.

2. The method according to claim 1, wherein said penetration enhancer is selected from the group selected from a group consisting of: alcohols, polyols, sulfoxides, esters, ketones, amides, oleates, surfactants, alkanoic acids, lactam compounds, alkanols, dialkylamino acetates, and mixtures thereof.

3. The method according to claim 1, wherein said alpha hydroxy acid is selected from the group consisting of lactic acid, glycolic acid, citric acid, mailc acid, decanoic acid, octanoic acid, tartaric acid, pyruvic acid, alpha-hydroxyethanoic acid, ammonium alpha-hydroxyethanoate, alpha-hydroxyoctanoic acid, alpha-hydroxyraprylic acid and hydroxycaprylic acid.

4. The method according to claim 1, further comprising coadministering at least one active ingredient is selected from the group consisting of lutein, zeaxanthin, nitric oxide synthase inhibitors, resveratrol, beta hydroxy acid, N-acetylcysteine, ascorbityl palmitate, ascorbic acid, alpha-lipoic acid, glutathione, methyl-sulfonyl-methane, zinc compounds, aloe vera, antioxidants, vitamins, ninerals, anino acids, and mixtures thereof, in a therapeutically acceptable vehicle.

5. The method according to claim 1 which further comprises additional agents selected from the group consisting of: oils (mineral, vegetable, animal and synthetics), glycols, preservatives, stabilizers, emollients, anti-infective agents, adjuvants, thickening and gelling agents, anthocyanidins, proanthocyanidins, amino sugars, glycosaminoglycans, colorants, gums, esters, hormones, silicones, polymers, fragrances, sunscreens, acids, bases, buffers, salts, proteins and their derivatives, essential oils, enzymes, co-enzynes and extracts, detergents, soaps, anionics, non-ionics, ionics, waxes, lipids, fillers, celluloses, amines, thickeners, sugars, manganese, magnesium, histidine, herbal derivatives, and mixtures thereof.

* * * * *